United States Patent [19]

Sylvanowicz

[11] Patent Number: 4,935,017
[45] Date of Patent: Jun. 19, 1990

[54] VARIABLE SHAPED CATHETER SYSTEM AND METHOD FOR CATHETERIZATION

[75] Inventor: John T. Sylvanowicz, Andover, Mass.

[73] Assignee: C. R. Bard, Inc., Murray Hill, N.J.

[21] Appl. No.: 188,046

[22] Filed: Apr. 29, 1988

[51] Int. Cl.⁵ .......................................... A61M 25/00
[52] U.S. Cl. ................................. 604/280; 604/53; 604/281
[58] Field of Search ................ 604/281, 43, 280, 264, 604/53, 95, 171, 158, 164; 128/657, 772

[56] References Cited

U.S. PATENT DOCUMENTS

| | | | |
|---|---|---|---|
| 3,856,009 | 12/1974 | Winnie | 604/281 |
| 4,033,331 | 7/1977 | Guss et al. | 604/281 |
| 4,136,681 | 1/1979 | Hon | 604/171 |
| 4,169,464 | 10/1979 | Obrez | 604/281 |
| 4,563,181 | 1/1986 | Wijayarathra et al. | 604/286 |
| 4,694,238 | 9/1987 | Wijayarthna et al. | 604/281 |
| 4,738,667 | 4/1988 | Galoway | 604/281 |
| 4,795,434 | 1/1989 | Kujawski | 604/164 |
| 4,810,244 | 3/1989 | Allen | 604/164 |
| 4,828,550 | 5/1989 | Kurimoto | 604/171 |

FOREIGN PATENT DOCUMENTS 0278937 8/1988 European Pat. Off. ............ 604/281

*Primary Examiner*—C. Fred Rosenbaum
*Assistant Examiner*—Kathleen A. Daley
*Attorney, Agent, or Firm*—Wolf, Greenfield & Sacks

[57] ABSTRACT

A catheter assembly and method for catheterization provides a means by which the curved configuration at the distal portion of a catheter can be varied while the catheter system remains in the patient. The catheter, having a predetermined curve at its distal end is received within a sheath that can be advanced over the distal end to tend to straighten the curve in the distal end of the catheter. The extent to which the sheath is advanced over the curved distal portion of the catheter controls the degree to which the catheter is straightened. The position of the sheath relative to the catheter can be adjusted while the catheter is in the patient, thereby enabling change in catheter shape without requiring catheter exchanges. For example, the system enables right and left coronary angiographic procedures to be performed without changing catheters. Left ventricular studies also can be made without catheter exchanges.

21 Claims, 1 Drawing Sheet

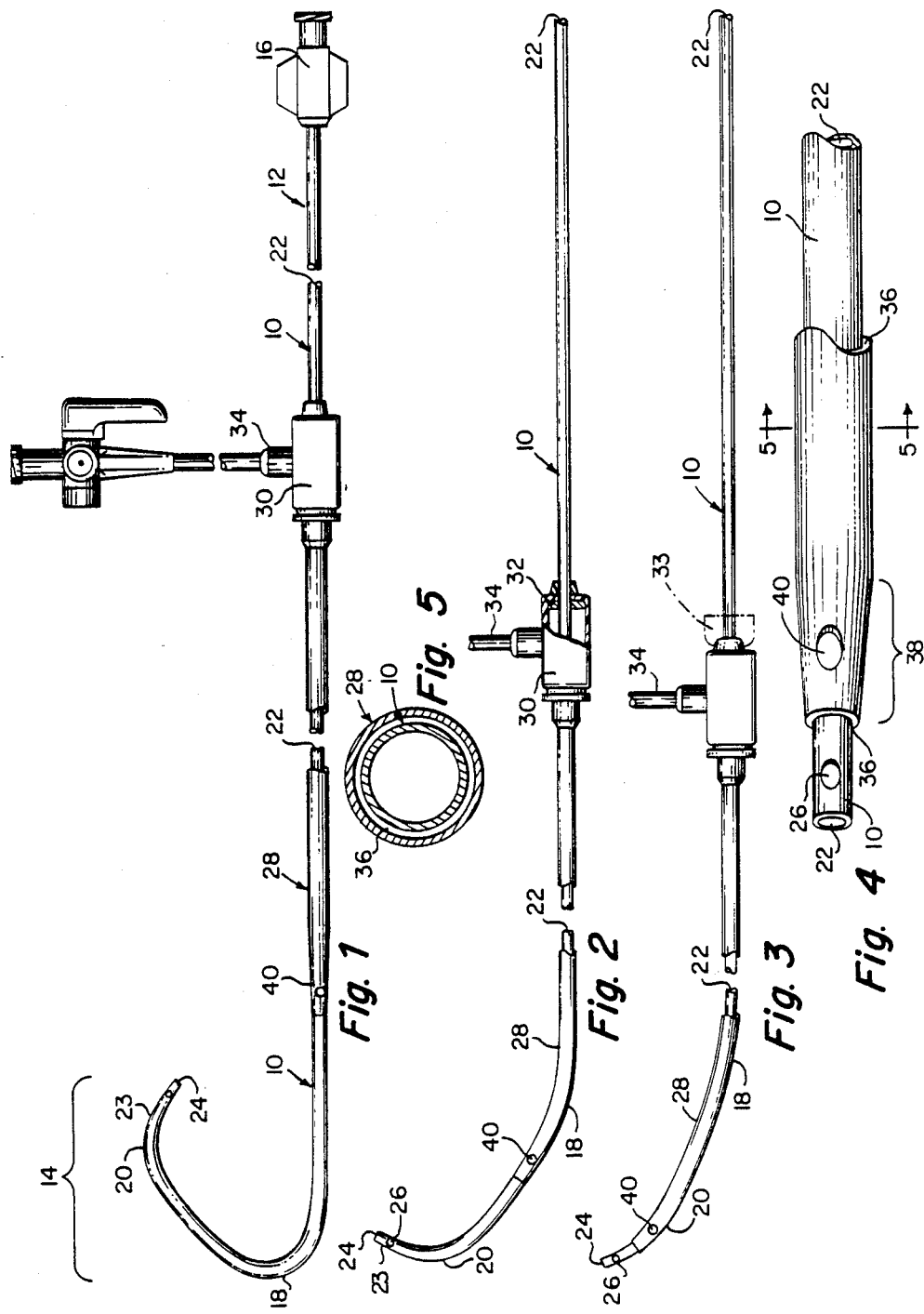

VARIABLE SHAPED CATHETER SYSTEM AND METHOD FOR CATHETERIZATION

FIELD OF THE INVENTION

This invention relates to improved angiographic and cardiovascular catheter systems and methods of catheterization.

BACKGROUND OF THE INVENTION AND PRIOR ART

For many years it has been the common practice in angiographic and cardiovascular procedures to use various angiographic catheters having different distal tip shapes in order to perform various angiographic studies. For example, when performing coronary angiography, it is common to perform studies of the left coronary artery, the right coronary artery, and the left ventrical by injecting X-ray opaque contrast liquid into each of the right and left coronary arteries and also into the left ventrical. Each injection is done with a separate catheter having a specially formed distal tip adapted to facilitate entry into the ostium of the right or left coronary artery. Typically, a catheter having a pigtail shape is used for left ventricular studies. In order to perform these studies it has been the typical practice to exchange catheters for each study. That is time consuming and subjects the patient to the trauma of multiple catheter insertion and removal. Additionally, the use of multiple catheters increases the risk of a blood clots and, in general, presents greater risk for complications.

The desirability of reducing the time involved in performing such angiographic studies as well as minimizing trauma to the patient by making a catheter having a tip shape adjustable while in the patient has been suggested in the prior art. U.S. Pat. No. 4,033,331 to Guss discloses a specially formed catheter having two lumens, including a main lumen through which the radiopaque contrast liquid may be injected into the blood vessel and another lumen which receives a relatively stiff elongated contour wire. The distal end of the catheter has a predetermined curved shape which can be progressively straightened by advancing the contour wire distally through its lumen. The system discussed in the Guss patent has several disadvantages, the principal one being that it cannot be used with a conventional angiographic catheter. The practice of the technique disclosed in the Guss patent requires the use of the special two lumen catheter construction. Additionally, that catheter construction necessarily has reduced flow area in the main lumen because of the necessity of providing the cross-sectional area for the contour wire lumen. In that regard, it is important to maintain a large flow area as possible in an angiographic catheter so that the radiopaque contrast liquid can be injected at a relatively high flow rate. With the two lumen catheter construction this desirable feature of such catheters is compromised.

SUMMARY OF THE INVENTION

In accordance with the present invention an angiographic catheter assembly is provided which includes a flexible angiographic catheter of conventional construction having a full size lumen and a pre-shaped curve at its distal end. The catheter extends through a sheath that is several centimeters shorter than the catheter, by an amount at least as great as the length of the curved distal segment of the catheter. The shape of the curve at the distal end of the catheter can be varied by advancing the sheath over the catheter. The sheath has sufficient stiffness so that it tends to straighten the catheter curve as it advances over it, thereby progressively changing the shape of the curve. The catheter assembly enables a method of angiography by which different procedures can be performed on the patient without requiring catheter exchanges for each procedure.

In another aspect of the invention, the sheath also may be used to deliver fluids or make pressure measurements at the distal tip of the sheath. To this end the proximal end of the sheath may be provided with a fitting having a side leg for liquid infusion. The inner diameter of the sheath may be somewhat larger than the outer diameter of the catheter to define an annular flow space along the length of the assembly. It is desirable that the distal tip of the sheath fit closely to the outer diameter of the catheter, the tip of the sheath being tapered for this purpose. In order to provide for fluid communication at the distal end of the sheath, the sheath may be provided with several side holes at its distal end. In addition, the sheath may be used as an introducer should it be desired to remove the catheter and replace it with another catheter.

The system is used in a method in which the relative position of the sheath on the catheter is selected to place the distal end of the catheter in a particular curved configuration suited for the angiographic procedure to be performed. After the dye injection and procedure have been completed, the longitudinal position of the sheath with respect to the catheter may be adjusted either to increase or decrease the curvature at the distal end or to permit the catheter to assume its more curved relaxed configuration, depending on which procedure is next to be performed. The change in configuration is effected quickly and simply with no additional trauma to the patient and without increasing the risk of complications that may result from a succession of catheter exchanges.

It is among the general objects of the invention to provide an improved catheter system for performing multiple cardiovascular and angiographic procedures while minimizing or reducing catheter exchanges.

Another object of the present invention is to provide a catheter system and method for catheterization by which the curvature at the distal end of a cardiovascular or angiographic catheter may be adjusted quickly and simply while within the patient.

Another object of the invention is to provide a system of the type described which utilizes a conventional angiographic catheter having a full size flow lumen.

A further object of the invention is to provide a catheter system of the type described in which the degree of curvature at the distal region of the catheter is controlled by a sheath that is slidably received over the catheter and which can be advanced or withdrawn over the catheter.

Another object of the invention is to provide a system of the type described in which means are provided for injecting radiopaque contrast liquid and making pressure measurements at the distal end of the sheath.

A further object of the invention is to provide system of the type described in which the sheath also may serve as a catheter introducer should it be desired to make a catheter exchange.

DESCRIPTION OF THE DRAWINGS

The foregoing and other objects and advantages of the invention will be appreciated more fully from the following further description thereof, with reference to the accompanying drawings wherein:

FIG. 1 is a fragmented illustration of the catheter system in accordance with the invention.

FIG. 2 is an illustration of the system with the sheath advanced distally over the primary curve in a Judkins left coronary catheter;

FIG. 3 is an illustration similar to FIG. 2 but with the sheath advanced over the secondary curve of the angiographic catheter;

FIG. 4 is an enlarged illustration of the distal end of the sheath and catheter; and FIG. 5 is a sectional illustration as seen along the line 5—5 of FIG. 4.

DESCRIPTION OF THE PREFERRED EMBODIMENT

The system illustrated includes an angiographic catheter 10 having a proximal end 12 and a distal end 14. The proximal end is provided with a fitting 16 which can be connected to a syringe for injecting radiopaque contrast liquid through the catheter 10 and into the patient. The distal end 14 of the catheter 10 is formed to define a predetermined curvature and, in the illustrative embodiment, the curvature is that conventionally known as the left Judkins curve, adapted for use in left coronary artery angiography. The left Judkins shape may be considered as having a primary curve 18 and a secondary curve 20. A lumen 22 extends fully through the angiographic catheter 10, from the fitting 16 to the distal outlet tip 24. The lumen 22 is full diameter, that is, it is uncompromised by the presence of any other elements in the catheter. The construction of the catheter 10 may be conventional as will be appreciated by those skilled in the art. For example, the catheter may be formed from extruded plastic material and may have woven or braided elements embedded in the catheter wall. By was of example the catheter may be approximately 125 centimeters in length although the length may be varied depending on the specific type of angiographic or cardiovascular procedure that is to be employed. If desired, the distal tip of the angiographic catheter 10 also may be provided with side holes 26 to increase outlet capacity. Typically, the tip of the catheter 10 will be tapered as indicated at 23 so that it may fit closely about a guidewire extending through the lumen 22 for smooth percutaneous entry, as will be appreciated by those familiar with the art.

The system of the present invention also includes an outer sheath indicated generally by the reference character 28 through which the catheter 10 extends. The sheath is circular in cross-section, as is the catheter 10, and may be formed from an appropriate extruded tube, such as FEP or PTFE fluorinated polymer. The sheath 28 is several centimeters shorter than the catheter 10, by an amount at least equal to the length of the curved distal portion 14 of the catheter 10. In the illustrative embodiment, the sheath is between 5 and 30 centimeters, preferably approximately 10 centimeters shorter than the catheter. Typically, the sheath length will be between 30 to 150 cm, depending on the length of the catheter. The proximal end of the sheath may be provided with a hemostasis fitting 30 that receives the catheter 10 and includes an internal proximal gasket 32 (FIG. 2) that engages the outer surface of the catheter 10 to form a seal against the catheter 10. The fitting 30 may be provided with an adjustable gasket such as a Tuohy-Borst adapter (illustrated in phantom at 33 in FIG. 3) by which the constricting force of the gasket about the catheter may be varied thereby to vary the degree with which the gasket seals against the catheter. The fitting 30 also may be provided with a side leg 34 through which liquids may be injected, pressure measurements may be made and sampling performed. The side leg on the sheath fitting also may be used to aspirate if there is to be a catheter exchange, in order to withdraw embolisms, or to inject heparin.

The sheath is formed so that when it is advanced over the curved distal portion 14 of the catheter 10, the stiffness of the sheath will cause the curve in the angiographic catheter 10 to become somewhat straighter. To this end, the sheath should be formed from a material and should have a wall thickness and stiffness sufficient to cause the catheter to assume the particular desired shape. FIG. 2 shows a sheath in an extended position in which it has been advanced over the primary curve 18 of the Judkins left catheter. In this configuration, the catheter is suited somewhat for a right coronary arteriography procedure. FIG. 3 illustrates the configuration of the system with the sheath advanced over both the primary and the secondary curves 18, 20 respectively. In this configuration, the assembly is best suited for an arteriography of coronary artery by-pass or for left ventriculography in the angiographic procedure. By way of example the catheter 10 may be between about 0.052 to about 0.117 (4F to 9F) in outer diameter and may be formed from polyurethene material with a braided tubular element embedded therein. The sheath preferably is formed from a tube of Teflon fluorinated polymer also in a 4F to 9F size with an inside diameter to match and receive the catheter. The sheath also preferably is radiopaque, as by incorporating barium sulfate or some other suitable radiopaque material into the polymer.

FIGS. 4 and 5 illustrates a tip construction for the sheath in which the sheath is adapted to provide fluid communication between its proximal and distal ends while receiving the catheter. In this embodiment the inner diameter of the sheath is somewhat larger than the outer diameter of the catheter to define an annular flow area 36 that communicates with the side leg 34. In the illustrated embodiment the tip of the sheath is tapered as indicated at 38 and fits closely against the outer surface of the catheter 10 to facilitate percutaneous introduction of the entire systems as a unit into the patient's blood vessel. One or more side holes 40 may be formed adjacent the tip of the sheath to provide for fluid communication with the annular area 36. The foregoing arrangement enables infusate to be delivered, pressure recordings to be made as well as sampling and purging. It may be noted that the distal portion of the sheath may have a straight configuration when relaxed or itself may be provided with a pre-formed curve.

The foregoing system also enables pressure differentials to be measured across a patient's aortic valve. By locating the system so that the distal tip of the catheter is located distally of the aortic valve and with the side holes 40 at the distal end of the sheath 28 located proximally of the aortic valve, pressure measurements can be made on both sides of the valve thereby providing an indication of the pressure differential.

From the foregoing it will be appreciated that the system may be percutaneiously introduced and used by advancing into the patient's blood vessels in a conventional manner as is well known to those skilled in the art. The sheath may be positioned along the catheter to present the desired curved configuration for the first study to be performed. After that study is performed the relative position of sheath and catheter may be adjusted to change the configuration of the catheter distal curve without requiring catheter exchanges. Dye injections and pressure measurements also may be made through the side leg 34 of the sheath if desired. Should it be desired to perform catheter exchanges that is facilitated by the sheath which may be permitted to remain in the patient's blood vessel thereby to serve as a catheter introducer. The system utilizes a full bore conventional angiographic catheter and thus permits full flow of radiopaque contrast liquid into the patient's blood vessels.

It should be understood that the foregoing description of the invention is intended to be illustrative and that other modifications and embodiments may be apparent to those skilled in the art without departing from its spirit and scope as set forth in the appended claims.

Having thus described the invention what I desire to claim and secure by letters patent is:

1. A variable shaped angiographic catheter assembly comprising;
    flexible elongated catheter having a proximal end and a distal end, and a distal portion formed to a predetermined curved shape;
    a flexible sheath having a proximal end, a distal end and an internal diameter adapted to receive the catheter and to enable longitudinal movement of the catheter within the sheath, the sheath being shorter than the catheter by an amount at least as great as the length of the curved distal portion of the catheter, the sheath having a degree of flexibility with respect to the catheter such that when the sheath is advanced over the curved portion of the catheter, the distal portion of the catheter and the sheath together assume a curve that is a less curved configuration whereby the shape of the curve at the distal end of the catheter can be controlled by adjusting the longitudinal position of the sheath with respect to the catheter.

2. A catheter assembly as defined in claim 1 further comprises;
    the catheter having a lumen extending from its proximal to its distal end and being open at its distal end and a fitting on the proximal end of the catheter in communication with the proximal end of the lumen for connection to a fluid instrumentality.

3. A catheter assembly as defined in claim 1 wherein the catheter comprises a coronary angiographic catheter.

4. A catheter assembly as defined in claim 1 wherein said catheter has a Judkins left curve formed in the distal portion.

5. A catheter assembly as defined in claim 1 wherein said sheath is approximately 5 to 30 centimeters shorter than the catheter.

6. A catheter assembly as defined in claim 1 further comprising:
    the internal diameter of the sheath being greater than the outer diameter of the catheter thereby to define an annular space extending along the length of the assembly;
    the distal end of the sheath being tapered to merge smoothly with and to contact the outer diameter of the catheter;
    at least one side hole formed at the distal portion of the sheath;
    a fitting at the proximal end of the sheath in communication with the annular flow space for connection to a fluid instrumentality.

7. A catheter assembly as defined in claim 1 further comprises;
    a fitting on the proximal end of the sheath, the catheter extending through the fitting, the fitting having a gasket adapted to contact and seal the periphery of the catheter.

8. A catheter assembly as defined in claim 7 wherein the seal is adjustable thereby to vary the degree with which the gasket seals against the catheter.

9. A variable shaped catheter assembly as defined in claim 1 wherein the sheath is dimensioned so that it contacts the outer surface of the catheter in close sliding contact therewith.

10. A catheter assembly as defined in claim 9 wherein the sheath is formed from a low friction polymeric material.

11. A catheter assembly as defined in claim 1 wherein the catheter is approximately 125 centimeters long and sheath is approximately 115 centimeters long.

12. A catheter assembly as defined in claim 11 wherein the catheter curve is formed to define a Judkins left shape.

13. A catheter assembly as defined in claim 1 wherein the catheter is an angiographic catheter.

14. A catheter assembly as defined in claim 1 wherein the catheter is a cardiovascular catheter.

15. A percutaneously insertable variable shaped angiographic catheter assembly as defined in claim 1 further comprising:
    the catheter having a lumen extending from its proximal to its distal end, the lumen being adapted to receive a guidewire;
    the distal tip of the catheter being tapered to merge smoothly with and to contact the outer diameter of a guidewire when a guidewire is received in the lumen;
    the distal tip of the sheath being tapered to merge smoothly with and to contact the outer diameter of the catheter whereby the assembly of the catheter and sheath may be inserted percutaneously into a blood vessel over a guidewire inserted into the blood vessel, said tapered portions forming self-dilating means.

16. A catheter assembly as defined in claim 1 or 15 in which the sheath is from a material having a high degree of radiopacity.

17. A method for performing an angiographic catherization comprising:
    providing a variable shaped angiographic catheter assembly including a flexible elongated catheter having a proximal end and a distal end, and a distal portion formed to a predetermined curved shape and a flexible sheath having a proximal end, a distal end and an internal diameter adapted to receive the catheter and to enable longitudinal movement of the catheter within the sheath, the sheath being shorter than the catheter by an amount at least as great as the length of the curved distal portion of the catheter, the sheath having a degree of flexibility with respect to the catheter such that when the sheath is advanced over the curved portion of the catheter, the distal portion of the catheter and the sheath together assume a curve that is a less curved configuration whereby the shape of the curve at the distal end of the catheter can be controlled by adjusting the longitudinal position of the sheath with respect to the catheter;

inserting said catheter assembly into a patient's cardiovascular system;

positioning the sheath of the assembly at a selected location to cause the distal end of the catheter to assume one curve with the catheter in that curve being adapted to perform a first angiographic catheterization procedure;

while maintaining the catheter in said first curve configuration, performing said first catheterization procedure;

thereafter shifting the position of the sheath with respect to the catheter thereby to change the curve at the distal end of the catheter to a second configuration adapted to perform a second angiographic catheterization procedure;

while maintaining said catheter in said second curve configuration, performing said second catheterization procedure.

18. A method as defined in claim 17 wherein said sheath and catheter define an annular lumen extending along the length of the sheath, the sheath having a proximal fitting for connection of a fluid device thereto, the procedure further comprising causing fluid to flow through the annular space defined the sheath and the catheter.

19. A method as defined in claim 17 wherein said sheath and catheter define an annular lumen extending along the length of the sheath, the sheath having a proximal fitting for connection of a fluid device thereto, the procedure further comprising measuring the fluid pressure in the patient's vasculature by connecting a fluid pressure measuring device to the proximal fitting of the sheath.

20. A method as defined in claim 17 wherein said catheter is directed to the entry to the patient's coronary arteries.

21. A method as defined in claim 17 further comprising:

advancing the catheter system to the aortic valve and locating the distal end of the catheter on one side of the aortic valve and the distal end of the sheath on the other side of the valve;

measuring the pressure distally and proximally of the aortic valve respectfully through the catheter and the sheath, thereby providing an indication of the pressure differential across the aortic valve.

* * * * *